US00PP26890P2

(12) United States Plant Patent
Williams

(10) Patent No.: US PP26,890 P2
(45) Date of Patent: Jun. 28, 2016

(54) ***COLOCASIA* PLANT NAMED 'DRAGON HEART'**

(50) Latin Name: ***Colocasia* hybrid**
Varietal Denomination: Dragon Heart

(71) Applicant: Brian Paul Williams, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 174 days.

(21) Appl. No.: 13/999,225

(22) Filed: Jan. 31, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Penny J. Aguirre

(57) ABSTRACT

A new cultivar of *Colocasia* plant named 'Dragon Heart' that is characterized by its large plant habit growing up to 2.1 m in height, its large leaves up to 90 cm in length, its velvety leaves that are very dark purple-black in color, its production of large tubers up to 15 cm in diameter, and its maroon petioles that are streaked with dark maroon and black.

2 Drawing Sheets

Botanical classification: *Colocasia* hybrid.
Cultivar designation: 'Dragon Heart'.

BACKGROUND OF THE INVENTION

The present invention, *Colocasia* 'Dragon Heart', relates to a new and distinct interspecific hybrid of *Colocasia*, hereinafter referred to by its cultivar name, 'Dragon Heart'. 'Dragon Heart' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Dragon Heart' arose from a cross make in June of 2010 between an unnamed plant of a *Colocasia* of hybrid origin from the Inventor's breeding program as the female parent and an unnamed plant of *Colocasia gigantea* as the male parent. 'Dragon Heart' was selected as a single unique plant in June of 2013 from amongst the seedlings derived from the above cross.

Asexual propagation of the new cultivar was first accomplished by in vitro propagation under the direction of the Inventor in Eustis, Fla. in November of 2013. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Dragon Heart' as a new and unique cultivar of *Colocasia*.

1. 'Dragon Heart' exhibits a large plant habit growing up to 2.1 m in height.
2. 'Dragon Heart' exhibits large leaves up to 90 cm in length.

3. 'Dragon Heart' exhibits velvety leaves that are very dark purple-black in color.
4. 'Dragon Heart' exhibits large tubers up to 15 cm in diameter.
5. 'Dragon Heart' exhibits maroon petioles that are streaked with dark maroon and black.

The female parent of 'Dragon Heart', an unnamed plant of *Colocasia* of hybrid origin, differs from 'Dragon Heart' in being shorter in height, in having smaller leaves, and in having smaller tubers. The male parent of 'Dragon Heart', an unnamed plant of *Colocasia gigantea*, differs from 'Dragon Heart' in having leaves and petioles that are green in color and in lacking large tuber production. 'Dragon Heart' can be most closely compared to the *Colocasia esculenta* cultivars 'Black Magic' (not patented) and 'Mojito' (U.S. Plant Pat. No. 21,995). Both are similar to 'Dragon Heart' in having large leaves. 'Black Magic' differs from 'Dragon Heart' in being shorter in height, in having petioles that are black in color, and in rarely producing tubers. 'Mojito' differs from 'Dragon Heart' in being shorter in height, in having leaves that are lime green in color with black variegation, in having petioles that are streaked black and green in color, and in rarely producing tubers.

BRIEF DESCRIPTION OF THE DRAWINGS

The accompanying colored photographs illustrate the overall appearance and distinct characteristics of the new *Colocasia*, 'Dragon Heart'. The photographs were taken of two year-old plants as grown outdoors in the garden in Louisville, Ky.

The photograph in FIG. 1 provides an overall view of the mature foliage and plant habit of 'Dragon Heart'.

Figure 1:
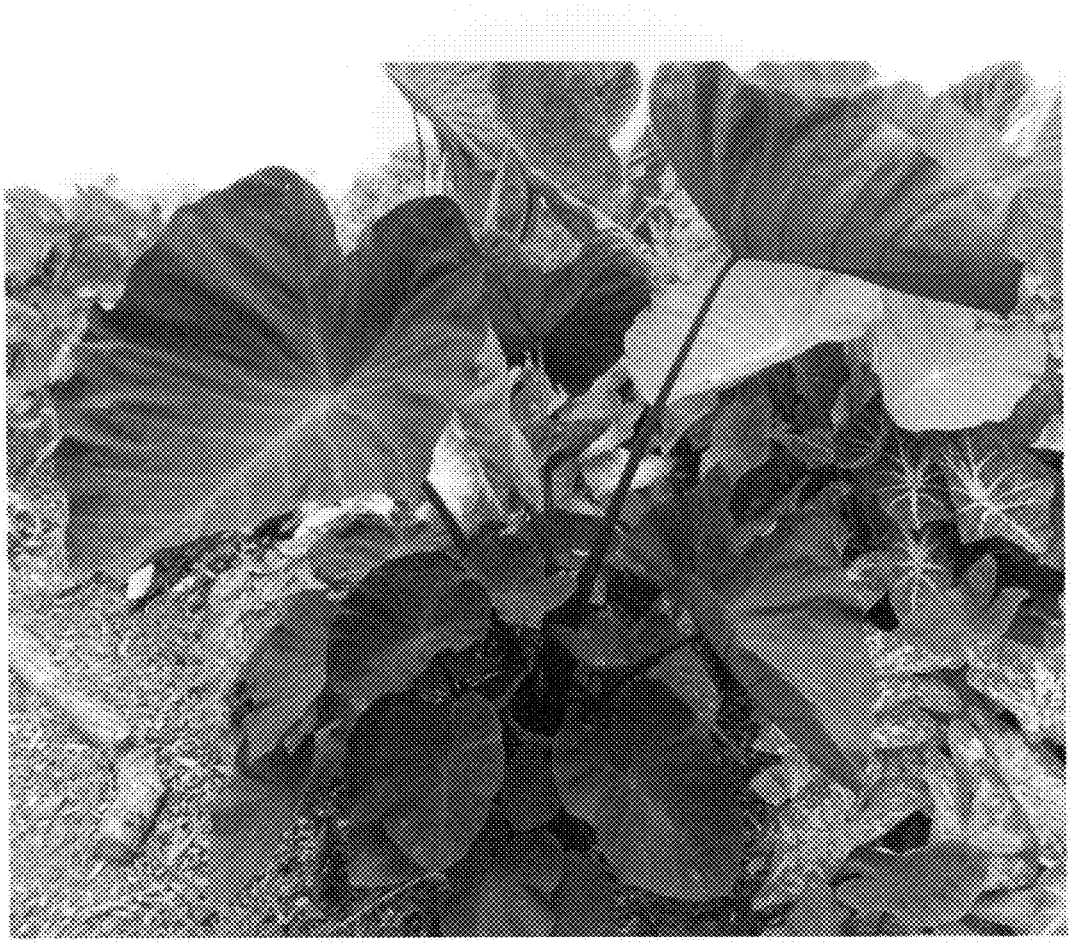
Figure 2:
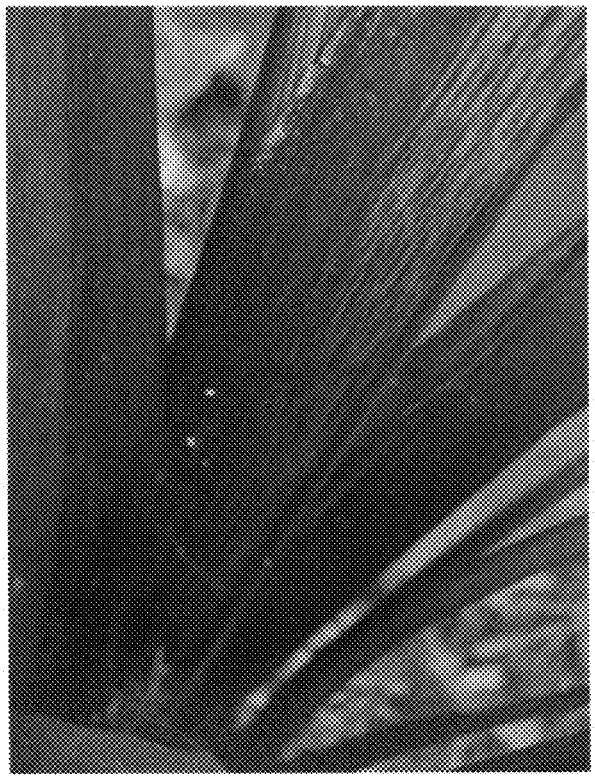

The photograph in FIG. 2 provides a close-up view of the petiole color of 'Dragon Heart'.

Figure 3:
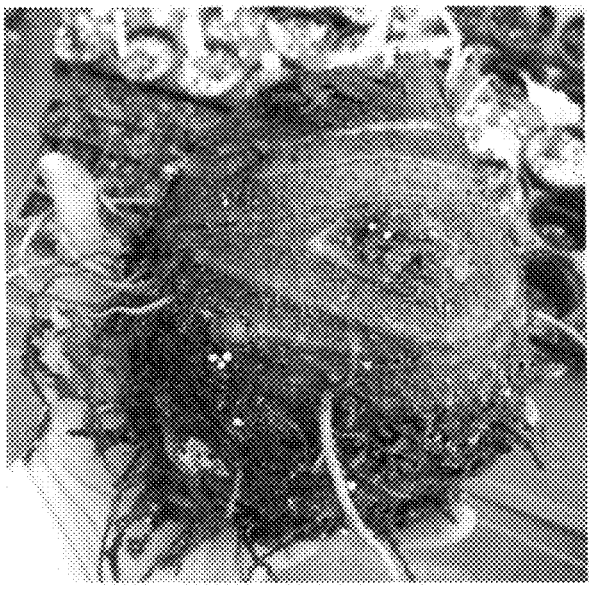

The photograph in FIG. 3 provides a close-up view of a large tuber of 'Dragon Heart'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of two year-old plants of the new cultivar as grown outdoors in a garden in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—August to September in Kentucky.

*Plant type.*—Tropical perennial herb.

*Plant habit.*—Upright, stemless.

*Height and spread.*—Reaches up to 2.1 m in height and 1.5 m in width.

*Cold hardiness.*—At least to U.S.D.A. Zone 7.

*Diseases.*—No resistance or susceptibility to diseases or pest has been observed.

*Roots.*—Fleshy.

*Propagation type.*—In vitro propagation is preferred.

*Growth rate.*—Vigorous.

*Stem description.*—Stemless, can produce tubers with age.

Foliage description:

*Leaf shape.*—Ovate.

*Leaf division.*—Single.

*Leaf base.*—Cordate.

*Leaf apex.*—Acute and cuspidate.

*Leaf venation.*—Pinnate, color upper surface; 198A, color lower surface; 183A.

*Leaf margins.*—Entire and slightly undulate.

*Leaf attachment.*—Petiolate.

*Leaf arrangement.*—Alternate.

*Leaf surface.*—Upper surface and lower surface; Velvety.

*Leaf orientation.*—Held horizontal to petiole.

*Leaf color.*—Upper surface very young foliage; N137A, lower surface very young foliage; 138B, upper surface mature foliage; a blend of N92 and 202A, lower surface mature foliage; N187C.

*Leaf size.*—Up to 90 cm in length and 61 cm in width.

*Petioles.*—Held erect to semi-erect, an average of 1.5 m in length and 3 cm in distal diameter and 5 mm in proximal diameter, satiny surface, color; 187A to 187C fading 159B lightly suffused with 187A to 187C at the top near the leaf attachment, tuber-like trunk formed at the base of the petioles with age; up to 15 cm in diameter, a blend of 187B and 187C with streaks of 187A and 202A, surface is comprised of petiole scales and bark-like.

Inflorescence description:

*Inflorescence type.*—Spadix surrounded by a spathe.

*Inflorescence size.*—Average of 42.5 cm in length and 4 cm in diameter.

*Inflorescence bud.*—Linear to slightly narrow oblanceolate in shape, an average of 23 cm length and 7 cm in width, a blend of 76C, N77A, N77C and N77D in color.

*Flower fragrance.*—Fresh fragrant smell.

*Lastingness of inflorescence.*—Inflorescence blooms intermittently during the bloom period, individual flowers last about 2 to 3 weeks.

*Inflorescence/flower quantity.*—Intermittent throughout the bloom season, an average of 110 female flowers per spadix, male flowers were undeveloped.

*Spathe.*—Hooded, bract, subtending spadix, elliptic in shape, entire margin, obtuse apex, coriaceous and slightly ribbed surface, 19 cm in length and 5 cm in width, lasts 5 to 7 days, color outside; a blend of 76C, N77A, N77C and N77D, color inside a blend of 76C, N77A, N77C and N77D fading to a blend of 151A, 159A with streaks of N77B.

*Spadix.*—Male portion above female zone, upright cylindrical shape (phallus-like), apex narrowly pointed, about 1.5 cm in diameter (not including ovary) and 13 cm in length, male zone; 10 cm in length and 7 mm in width, color immature and mature a blend of 159C and N187A, female zone; 3 cm in diameter and length, color immature and mature a blend of N187A and 145A.

*Peduncle.*—Emerges from base of plant, up to 19 cm in length and 6 cm in diameter, held upright, a blend of N77A and N77C in color, glaucous surface.

Reproductive organs:

*Gynoecium.*—Stigmas are 150C in color, ovary is round in shape and 150C in color.

*Androcoecium.*—Undeveloped.

*Fruit and seed.*—Sterile.

It is claimed:

1. A new and distinct cultivar of *Colocasia* plant named 'Dragon Heart' as herein illustrated and described.

* * * * *